Dec. 23, 1958 G. MERRILL Plant Pat. 1,785
PEACH
Filed April 25, 1958
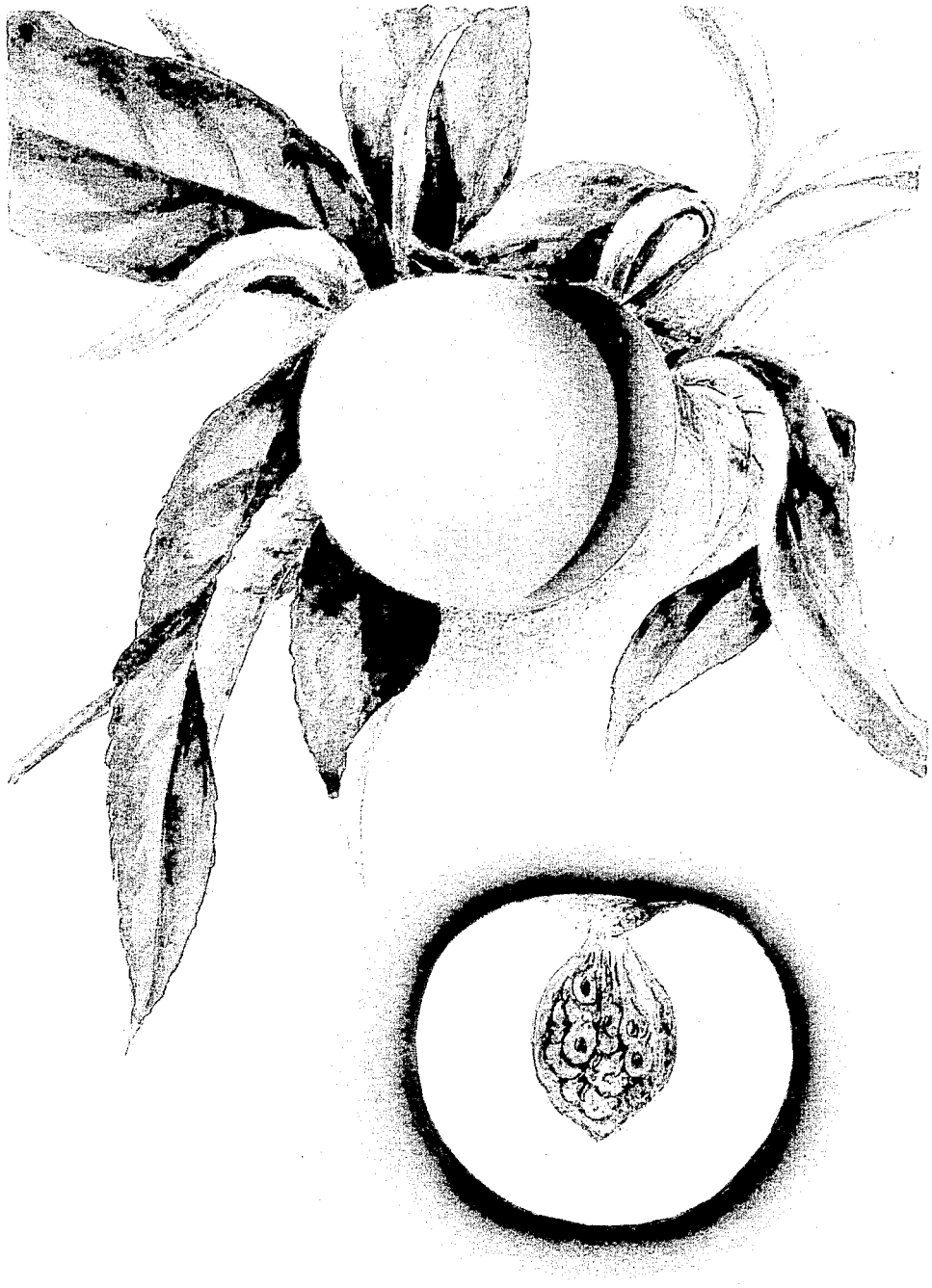
WITNESS
Addison E. Avery
INVENTOR
GRANT MERRILL United States Patent Office Plant Pat. 1,785

Patented Dec. 23, 1958

1,785

PEACH

Grant Merrill, Red Bluff, Calif., assignor to Grant Merrill Orchards, Inc., Red Bluff, Calif., a corporation of California Application April 25, 1958, Serial No. 731,067

1 Claim. (Cl. 47—62)

This invention relates to a new and distinct variety of peach tree which bears highly colored, firm, large, yellow fleshed, freestone peaches, which are almost entirely covered with red, and on a productive tree and blooming moderately late.

A distinguishing feature of this peach is that it ripens during the early part of the gap between July Elberta (Plant Patent No. 15) and Elberta (unpatented), or about ten days ahead of Elberta (unpatented).

The fruit of the instant variety is additionally distinguished by its round shape, small suture ridge and small apical tip.

In comparison with Merrill Gemfree (Plant Patent No. 1,409), which the instant variety most nearly resembles, it ripens about forty days later, in Red Bluff, California, and the flesh is almost completely free from the pit when ripe, the skin is a brighter red and the tree blooms later.

I originated the instant variety of peach on my farm near Red Bluff, Tehama County, California, in the following manner.

Seeds were planted from four generations of open pollinated blossoms (F4) starting with J. H. Hale (unpatented) and selecting each time for high color, firmness, large size of fruit along with other good fruit and tree characteristics. In the fourth generation (F4), this selection, L–130, first fruited in August 1954, and was an improvement over its parent.

In September 1955, to asexually reproduce the instant variety buds were placed in some seedlings growing in a test plot on my above mentioned farm. These grew out in 1956 and 1957 and bore fruits which were identical to those of the original tree.

In the drawings the fruit is shown in elevation together with twigs and leaves and also sectional elevations of fruit with the stone exposed.

Referring now more specifically to the pomological details of this new and distinct variety of peach tree, the following is an outline description thereof; all major color plate identifications being by reference to Maerz and Paul Dictionary of Color.

*Tree*

Medium size, medium vigorous, medium upright, medium dense, vase formed by pruning, hardiness unknown, productive, regular bearer.

Trunk: Medium slender, medium shaggy.

Branches: Grey and shaggy when old, brown and fairly smooth when young. Lenticels—medium quantity, medium size.

Leaves (selected from midportion of vigorous unbranched terminal shoots, 18″ to 24″ long taken from the top of the tree):

*Length.*—6⅞″ to 8½″. Average, 7⅜″.

*Width.*—1 5/16″ to 1¾″. Average, 1 9/16″. Medium large, lanceolate, tip acuminate, medium thick.

*Color.*—Upper surface, green (22–L–8) to slightly more yellow. Under surface, green (21–J–7). Heavy under midrib, lighter green (10–I–1).

*Class* (Meader and Blake: Proceedings Am. Soc. Hor. Sc., vol. 27, page 206).—2, some 3, few 4. Width—length ratio .21. Apex angle, 31° to 39°; average, 35°. Base angle, 72° to 82°; average, 74°.

*Margin.*—Crenate.

*Petiole.*—Medium length, medium thick.

*Glands.*—Average 1 to 4, usually 2. Opposite and alternate. Medium size, reniform, usually light green, few darker, some red. Position usually on petiole, some on base of leaf.

*Stipules.*—At base of leaf falling off early.

Flower buds: Hardiness unknown, medium size, truncate to obtuse, plump, free, pubescent.

Flowers: Midseason to slightly late in bloom, pink, pollen moderate in amount.

*Fruit*

Maturity when described—firm ripe.

Size: Fairly uniform, medium to large. Axial diameter, 2½″ to 3″; average, 2¾″. Transverse to suture plane, 2½″ to 3″; average, 2¾″. At right angles to suture plane, 2½″ to 3″; average, 2¾″.

Form: Globose, slightly flattened at base and apex.

*Suture.*—Distinct, shallow, extends from base to beyond apex, has slight depression beyond pistil point.

*Ventral surface.*—Slightly lipped throughout on either side. Lips—unequal.

*Cavity.*—Abrupt, elongated in suture plane, with suture showing strongly on both sides. Depth, ½″ to ⅝″; average, 7/16″. Breadth, ½″ to ⅝″; average 9/16″. Markings—blush extends into cavity from none to 100%, background color, greenish yellow.

*Base.*—Retuse.

*Apex.*—Rounded to retuse.

*Pistil point.*—Apical.

*Stem.*—Length average, ½″. Diameter, ⅛″. Adheres to stone frequently.

*Skin.*—Medium thick, medium tough, frees from flesh when soft ripe; tendency to crack, none. Color—yellow (11–L–9) to orange yellow (3–E–12), bright red blush extends over almost entire surface varying from lighter red (4–L–10) to darkest red (7–L–6). Down—scant, short, does not roll up when rubbed.

Flesh: Light yellow (9–L–6) to darker yellow (9–L–7), with considerable red around the stone (5–L–6).

*Surface of pit cavity.*—Pink to red.

*Fibers.*—Pink.

*Amygadalin.*—Scant.

*Juice.*—Moderate.

*Texture.*—Fine, firm, meaty, melting when soft ripe.

*Fibers.*—Few, fine, tender.

*Ripens.*—Evenly.

*Flavor.*—Mild, subacid.

*Aroma.*—Distinct.

*Eating quality.*—Good to best.

Stone: Free, adheres to flesh slightly when firm ripe, along dorsal and ventral edges, completely free when soft ripe. Fibers few and short, parts from the flesh smoothly.

*Size.*—Medium length, 1⅜″ to 1½″; average, 1 7/16″. Breadth, 1″ to 1 3/16″; average, 1 3/32″. Thickness, 11/16″ to 13/16″; average, 25/32″.

*Form.*—Obovate, tip cuspidate in varying degrees.

*Base.*—Slightly oblique. Hilum—oval.

*Apex.*—Cuspidate.

*Sides.*—Some equal, some unequal, mostly curved.

*Surface.*—Mostly curved, irregularly furrowed near edges, pitted toward center. Ridges—jagged toward dorsal edge, pits irregular. Ventral edge—thick without wings or very subdued wings. Dorsal edge—narrower with deep to more shallow grooves throughout on either side, mostly interrupted.

*Color.*—Reddish to almost purple (7–C–6).

*Tendency to split.*—Little.

Use: Market, local, dessert, culinary, long distance shipping.

Keeping quality: Good.

Shipping quality: Good.

*General notes*

The tree and its fruit herein described may vary some due to climatic and soil conditions under which the variety may be grown, and the method of growing, including fertilizing, pruning, thinning, the pests and diseases present on the tree, and other causes.

The following is claimed:

A new and distinct variety of peach substantially as described and illustrated and producing large, highly colored, firm, yellow fleshed freestone peaches, almost entirely covered with red, round in shape, with small suture ridge, very small apical tip, characterized as to novelty by its ripening during the early part of the gap between July Elberta (Plant Patent No. 15) and Elberta (unpatented) or about ten days ahead of Elberta (unpatented) in Red Bluff, Tehama County, California, and being similar to Merrill Gemfree (Plant Patent No. 1,409) which the instant variety most nearly resembles, but ripening about forty days later in Red Bluff, Tehama County, California, and with flesh which is almost completely free from the pit, and with skin that is brighter red and with a tree that blooms a few days later.

No references cited.